(12) United States Patent
Franz et al.

(10) Patent No.: US 10,275,886 B2
(45) Date of Patent: *Apr. 30, 2019

(54) TUMOR SEGMENTATION AND TISSUE CLASSIFICATION IN 3D MULTI-CONTRAST

(71) Applicant: KONINKLIJKE PHILIPS N.V., Eindhoven (NL)

(72) Inventors: Astrid Ruth Franz, Hamburg (DE); Stefanie Remmele, Landshut (DE); Jochen Keupp, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/398,768

(22) Filed: Jan. 5, 2017

(65) Prior Publication Data

US 2017/0116747 A1 Apr. 27, 2017

Related U.S. Application Data

(63) Continuation of application No. 14/374,652, filed as application No. PCT/IB2013/050644 on Jan. 25, 2013, now Pat. No. 9,547,061.

(Continued)

(51) Int. Cl.
*G06K 9/00* (2006.01)
*G06T 7/11* (2017.01)
(Continued)

(52) U.S. Cl.
CPC .............. *G06T 7/11* (2017.01); *A61B 5/055* (2013.01); *A61B 5/742* (2013.01); *A61B 6/037* (2013.01);
(Continued)

(58) Field of Classification Search
CPC ... G06T 7/11; G06T 7/12; G06T 2207/20128; G06T 7/194; A61B 2576/026; G06K 9/0014; G06K 9/342
See application file for complete search history.

(56) References Cited

U.S. PATENT DOCUMENTS 6,697,497 B1 * 2/2004 Jensen ...................... G06T 7/12
382/100
7,336,809 B2 * 2/2008 Zeng ..................... G06T 7/0012
128/922

(Continued)

FOREIGN PATENT DOCUMENTS

CN 102521646 A 6/2012

OTHER PUBLICATIONS

Franz, A. et al "Semi-Automatic Intracranial Tumor Segmentation and Tumor Tissue Classification based on Multiple MR Protocols", Proceedings of SPIE, vol. 8314, Feb. 2012.

(Continued)

*Primary Examiner* — Bhavesh M Mehta
*Assistant Examiner* — Ian L Lemieux

(57) ABSTRACT

A medical imaging system (5) includes a workstation (20), a coarse segmenter (30), a fine segmenter (32), and an enclosed tissue identification module (34). The workstation (20) includes at least one input device (22) for receiving a selected location as a seed in a first contrasted tissue type and a display device (26) which displays a diagnostic image delineating a first segmented region of a first tissue type and a second segmented region of a second contrasted tissue type and identified regions which include regions fully enclosed by the first segmented region as a third tissue type. The coarse segmenter (30) grows a coarse segmented region of coarse voxels for each contrasted tissue type from the seed location based on a first growing algorithm and a growing fraction for each contrasted tissue type. The seed (Continued)

Figure 1:
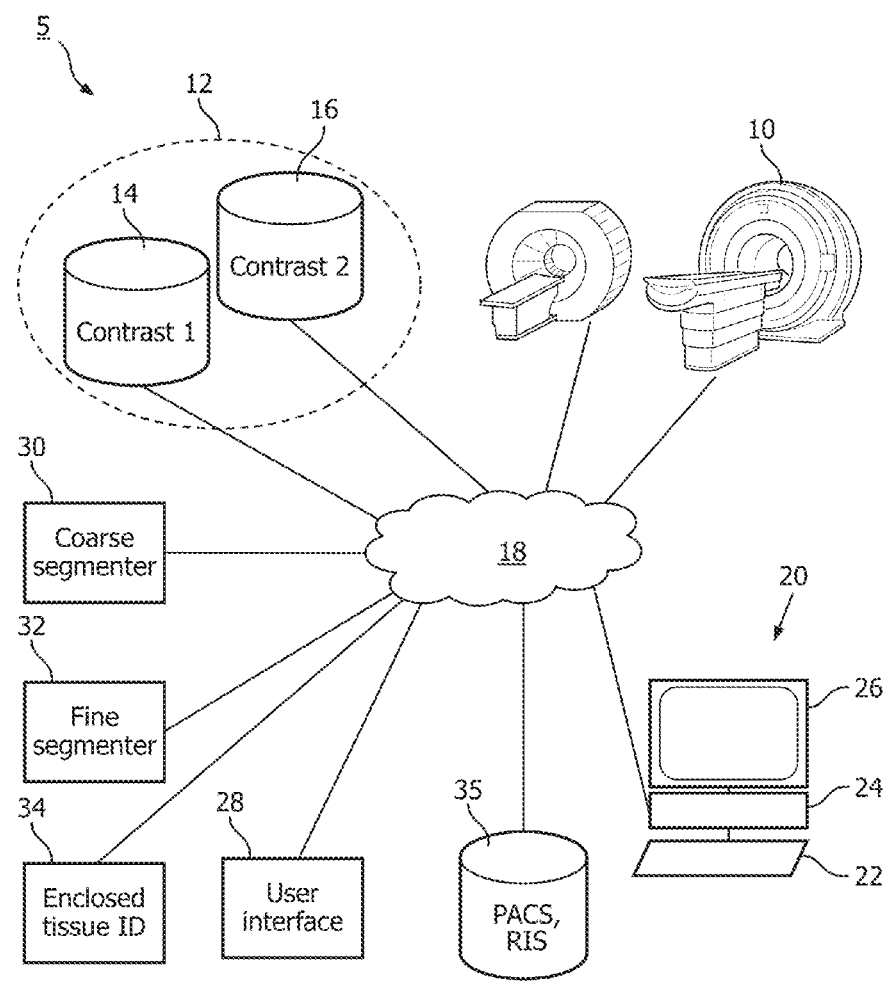

location for growing the second contrasted tissue type includes the first coarse segmented region and any fully enclosed coarse voxels, and each coarse voxel includes an aggregation of voxels and a maximum and a minimum of the voxel intensities. The fine segmenter (32) grows a segmented region of voxels for each contrasted tissue type from the seed location and bounded by the second coarse segmented region based on a second growing algorithm and a growing fraction for each contrasted tissue type initially set to the growing fraction for the corresponding region. The seed location for growing the second contrasted tissue type includes the first segmented region and any identified regions. The enclosed tissue identification module (34) identifies any regions of voxels fully enclosed by the first segmented region as being of the third tissue type. The coarse segmenter, the fine segmenter, and the enclosed tissue identification module are implemented by an electronic data processing device.

20 Claims, 7 Drawing Sheets

Related U.S. Application Data

(60) Provisional application No. 61/591,396, filed on Jan. 27, 2012.

(51) Int. Cl.
| | | |
|---|---|---|
| A61B 5/055 | (2006.01) | |
| A61B 6/00 | (2006.01) | |
| G01R 33/56 | (2006.01) | |
| G01R 33/563 | (2006.01) | |
| G06T 15/08 | (2011.01) | |
| G06T 7/174 | (2017.01) | |
| G06T 7/187 | (2017.01) | |
| A61B 5/00 | (2006.01) | |
| A61B 6/03 | (2006.01) | |
| G01R 33/48 | (2006.01) | |
| G06T 7/00 | (2017.01) | |

(52) U.S. Cl.
CPC ............ *A61B 6/461* (2013.01); *A61B 6/481* (2013.01); *A61B 6/5211* (2013.01); *G01R 33/4808* (2013.01); *G01R 33/5601* (2013.01); *G01R 33/563* (2013.01); *G06T 7/0012* (2013.01); *G06T 7/174* (2017.01); *G06T 7/187* (2017.01); *G06T 15/08* (2013.01); *A61B 5/0042* (2013.01); *G06T 2207/10088* (2013.01); *G06T 2207/10104* (2013.01); *G06T 2207/20016* (2013.01); *G06T 2207/20092* (2013.01); *G06T 2207/20168* (2013.01); *G06T 2207/30016* (2013.01); *G06T 2207/30096* (2013.01)

(56) References Cited

U.S. PATENT DOCUMENTS

| | | |
|---|---|---|
| 2008/0260221 A1 | 10/2008 | Unal |
| 2009/0208078 A1 | 8/2009 | Fritz |
| 2011/0058720 A1 | 3/2011 | Lu |
| 2011/0170759 A1 | 7/2011 | Bjornerud |
| 2011/0286654 A1 | 11/2011 | Krishhnan |
| 2013/0329973 A1* | 12/2013 | Cao ............ A61B 5/0033 382/128 |
| 2016/0005183 A1 | 1/2016 | Thiagarajan |
| 2017/0309025 A1* | 10/2017 | O'Rourke ............ G06T 7/0012 |

OTHER PUBLICATIONS

Bulow, T. et al "Segmentation of Suspicious Lesions in Dynamic Contrast-Enhanced Breast MR Images", Proceedings of SPIE, vol. 6514, Feb. 2007.
Franz, A. et al "Brain Tumour Segmentation and Tumour Tissue Classification based on Multiple MR Protocols", Medical Imaging 2011, vol. 7962, No. 1, Mar. 2011, pp. 1-6.
Opfer, Roland et al "Automatic Lesion Tracking for a PET/CT based Computer Aided Cancer Therapy Monitoring System", Medical Imaging 2008: Computer-Aided Diagnosis, Prog. of SPIE, vol. 6915, No. 691513.
Lorenz et al "Fast Automated Object Detection by Recursive Casting of Search Rays" in Proc. Cars, ICS 1281, pp. 230-235(2005).

* cited by examiner

TUMOR SEGMENTATION AND TISSUE CLASSIFICATION IN 3D MULTI-CONTRAST

This application is a continuation of U.S. patent application Ser. No. 14/374,652, filed Jul. 25, 2014, which is the U.S. National Phase application under 35 U.S.C. § 371 of International Application No. PCT/IB2013/050644, filed on Jan. 25, 2013, which claims the benefit of U.S. Provisional Patent Application No. 61/591,396, filed on Jan. 27, 2012. These applications are hereby incorporated by reference herein.

The following relates generally to medical imaging. It finds particular application in conjunction with segmenting tissue types in diagnostic imaging, and will be described with particular reference thereto. However, it will be understood that it also finds application in other usage scenarios and is not necessarily limited to the aforementioned application.

A frequent application of medical imaging is tumor diagnosis and grading. In grading a tumor, segmentation is used to identify vital tumor tissue, surrounding edema tissue, and any necrotic tissue completely enclosed by the vital tumor tissue. Tumor segmentation differs from organ segmentation which is facilitated by a model-based approach. A model-based approach works for organ segmentation because the anatomy of the body can be used as a guide. For example, many model-based approaches use an atlas in the segmentation process. However, tumors do not have a common form and do not have a common grey value structure. There are no anatomical models for tumors and therefore tumor segmentation cannot be based on anatomical models or a model-based approach.

Some algorithms for tumor segmentation attempt to differentiate tissue with boundary identification. Typically, these segmentation approaches use manual approaches based on geometric models or down sampling. Geometric models or down sampling use averages or interpolation for fast computational measurement of tumor boundaries which lose information, especially edge information. The edge information is important in segmenting the different tissue types involved with tumor staging identification such as vital tumor tissue, edema or peri-focal tissue, and necrotic tissue. The differentiation of tissue types is important in radiation therapy planning, surgical planning, tumor diagnosis and staging, evaluation of treatment outcome via volumetry, automatic region of interest (ROI) segmentation for quantitative analysis, etc. For example, radiation treatment typically focuses on vital tumor tissue. Necrotic tissue does not need radiation treatment because necrotic tissue is dead tissue. However, radiation treatment does not need to avoid necrotic tissue. Radiation treatments typically avoid peri-focal tissue which is at risk, but still viable tissue.

Another approach uses a growing algorithm with an adaptive upper bound. The upper bound is the grey value passed by the growing region, and the lower bound is chosen relative to the upper bound. However, controlling the growth to prevent leakage to small connecting bright bands of neighboring structures is problematic.

Additionally multiple images may be needed to contrast the different tumor tissue types. For example, an image with one contrast highlights vital tumor tissue while an image with a different contrast highlights edema tissue. Segmenting vital tumor tissue from edema tissue from normal tissue can be a difficult process, and local conditions can affect the contrast of the tissue types which is used for segmentation.

The following discloses a new and improved tumor segmentation and tissue classification which addresses the above referenced matters, and others.

In accordance with one aspect, a medical imaging system includes a workstation, a coarse segmenter, a fine segmenter, and an enclosed tissue identification module. The workstation includes at least one input device for receiving a selected location as a seed in a first contrasted tissue type and a display device which displays a diagnostic image delineating a first segmented region of a first tissue type and a second segmented region of a second contrasted tissue type and identified regions which include regions fully enclosed by the first segmented region as a third tissue type. The coarse segmenter grows a coarse segmented region of coarse voxels for each contrasted tissue type from the seed location based on a first growing algorithm and a growing fraction for each contrasted tissue type. The seed location for growing the second contrasted tissue type includes the first coarse segmented region and any fully enclosed coarse voxels, and each coarse voxel includes an aggregation of voxels and a maximum and a minimum of the voxel intensities. The fine segmenter grows a segmented region of voxels for each contrasted tissue type from the seed location and bounded by the second coarse segmented region based on a second growing algorithm and a growing fraction for each contrasted tissue type initially set to the growing fraction for the corresponding region. The seed location for growing the second contrasted tissue type includes the first segmented region and any identified regions. The enclosed tissue identification module identifies any regions of voxels fully enclosed by the first segmented region as being of the third tissue type. The coarse segmenter, the fine segmenter, and the enclosed tissue identification module are implemented by an electronic data processing device.

In accordance with another aspect, a method performs a coarse region growing algorithm to define a coarse segmented region in an image, the coarse region growing algorithm operating on coarse voxels of the image where each coarse voxel is an aggregation of voxels characterized in the coarse region growing algorithm by the maximum voxel value of the aggregation of voxels and the minimum voxel value of the aggregation of voxels. A fine region growing algorithm is performed to define a segmented region in the image, the fine region growing algorithm operating on voxels of the image and being constrained by a growth bound defined by the coarse segmented region. The segmented region is displayed on a display device. The performing operations are performed by an electronic data processing device.

In accordance with another aspect, a medical imaging system includes an electronic data processing device configured to perform operations including segmenting a T1 contrast enhanced (T1CE) magnetic resonance image of an imaging subject to define a segmented region comprising vital tumor tissue, and segmenting a fluid attenuated inversion recovery (FLAIR) magnetic resonance image of the imaging subject using region growing to define a segmented region comprising edema tissue. The segmented region comprising vital tumor tissue serves as the seed for the region growing.

One advantage is segmentation which retains tissue edge information.

Another advantage is the masking of regions of segmentation to prevent leakage of similarly contrasted, but unrelated tissue types.

Another advantage resides in the segmentation and identification of related tumor tissue types.

Another advantage resides in a user interface for fine tuning of the segmented tissue.

Still further advantages of the present application will be appreciated to those of ordinary skill in the art upon reading and understanding the following detailed description.

FIG. 1 schematically illustrates an embodiment of the medical imaging system.

Figure 2A:
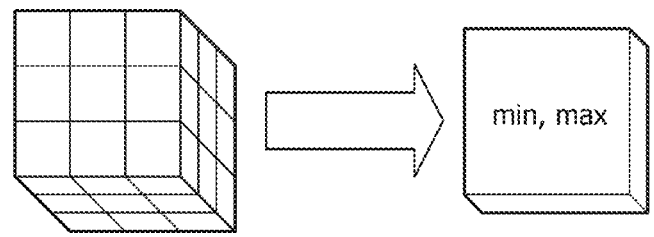
Figure 2B:
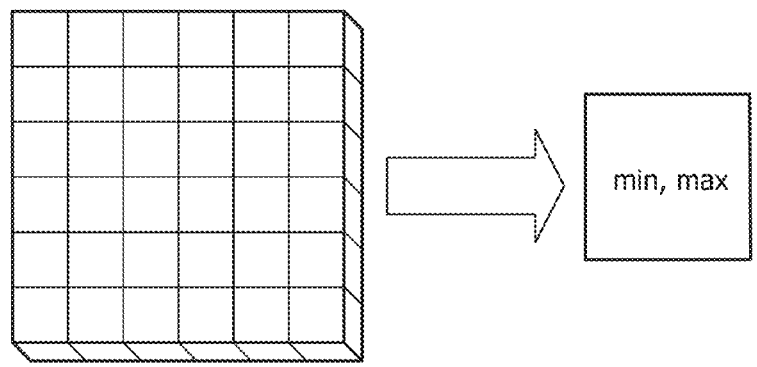

FIG. 2A-B schematically illustrates several examples of coarse voxel construction performed by the coarse segmenter.

Figure 3:
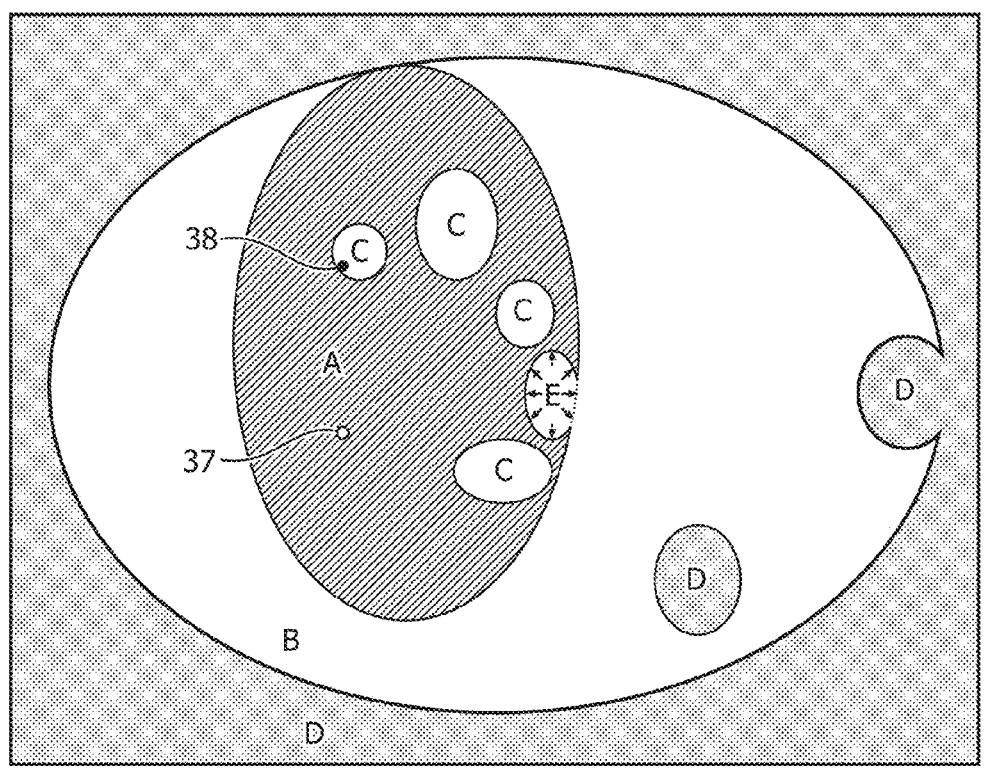

FIG. 3 diagrammatically illustrates an example of the various segmented and identified regions.

Figure 4:
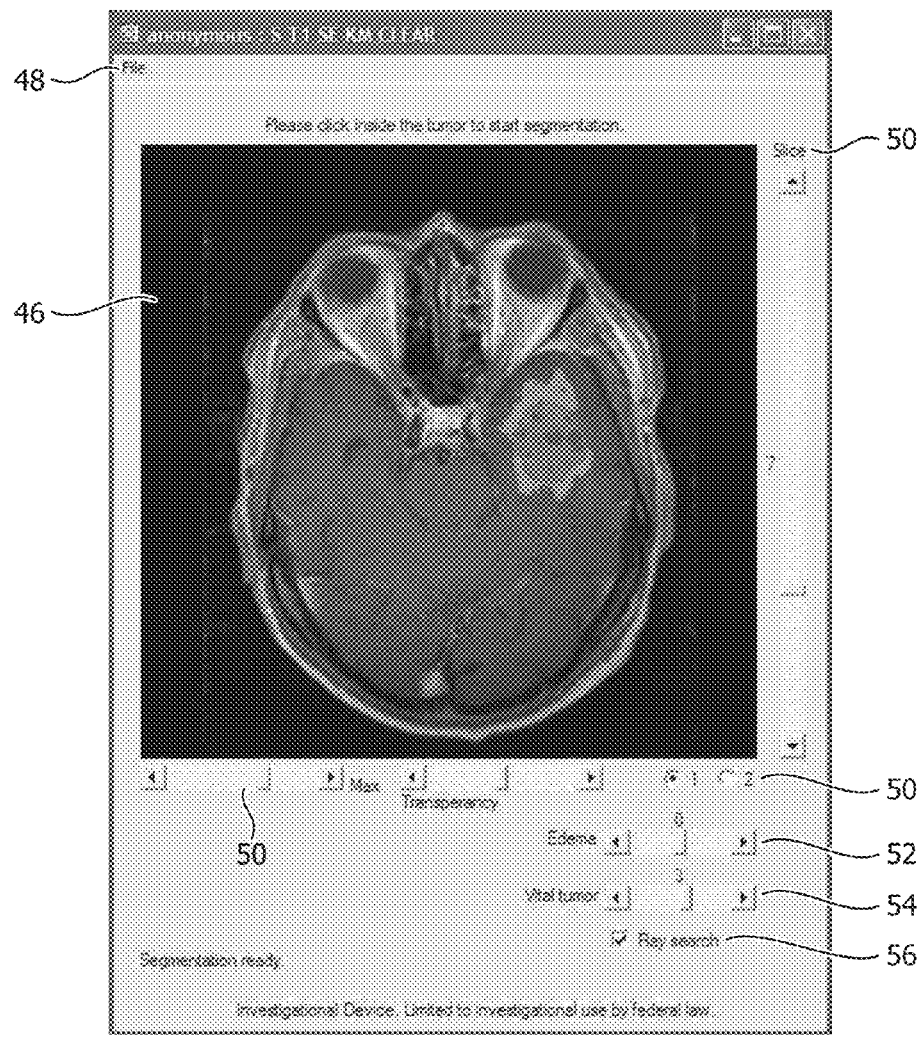

FIG. 4 illustrates an example user interface.

Figure 5:
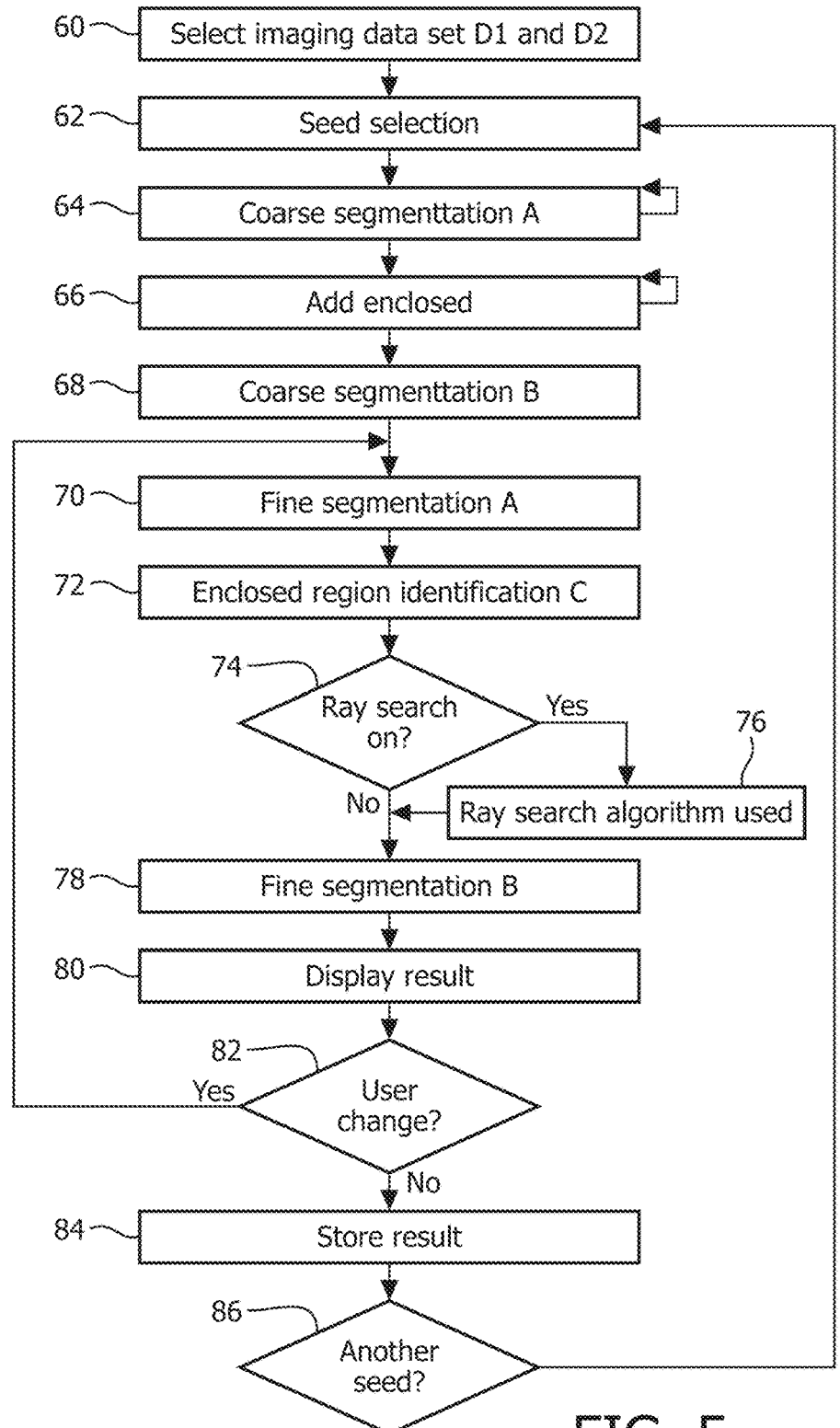

FIG. 5 flowcharts one method of using an embodiment of the segmentation and tissue identification.

Figure 6:
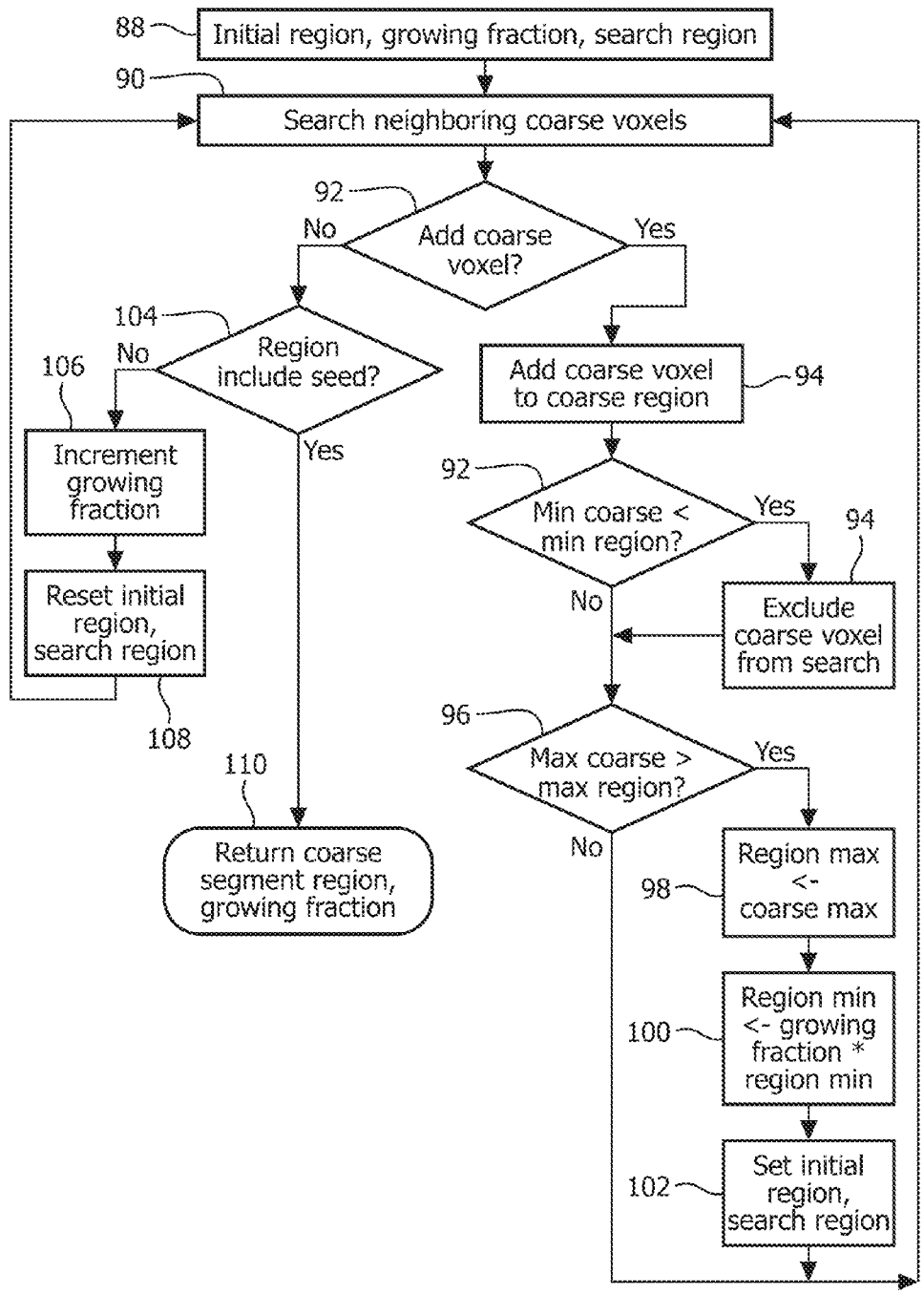

FIG. 6 flowcharts one method of the coarse segmentation growing algorithm.

Figure 7:
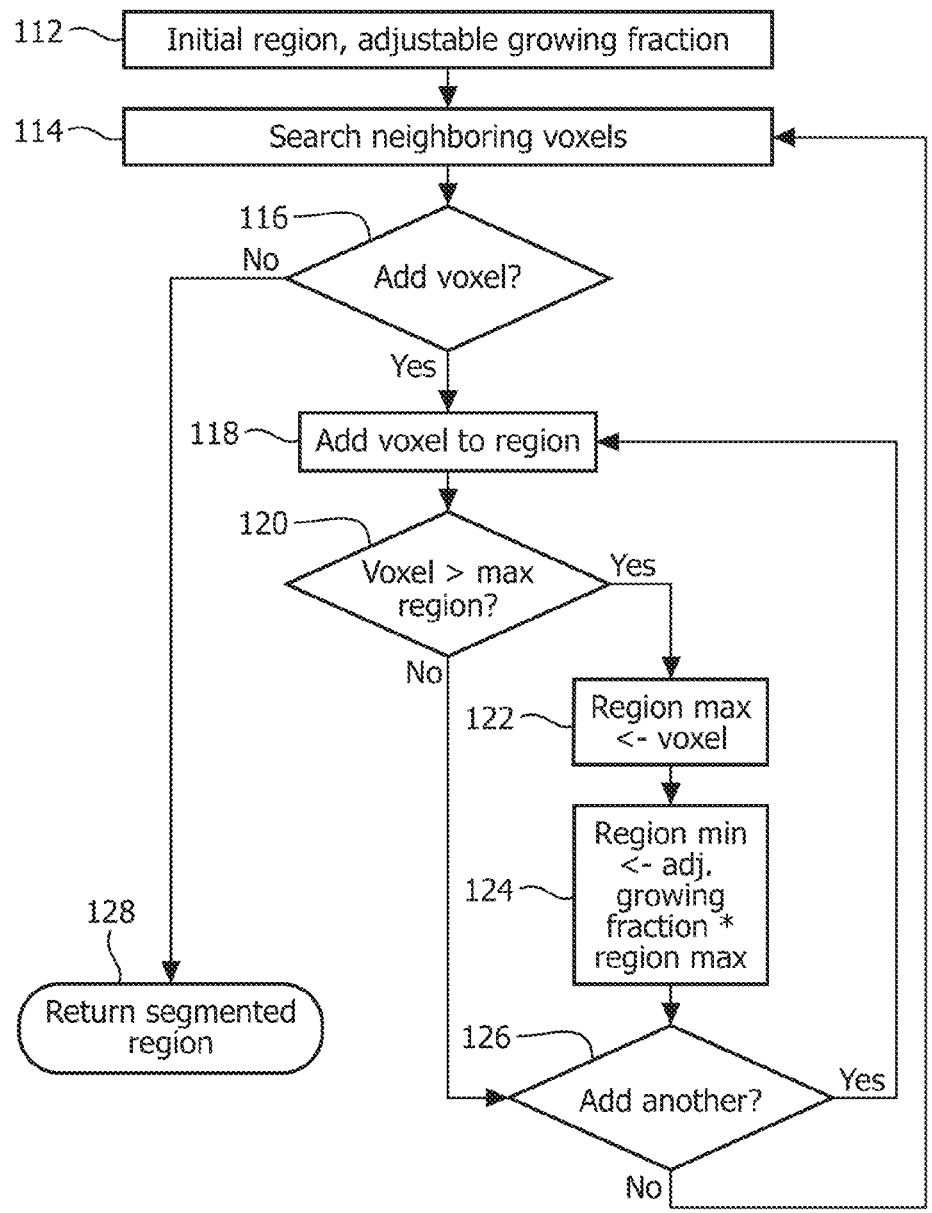

FIG. 7 flowcharts one method of the fine segmentation growing algorithm.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of the medical imaging system 5. One or more medical images are generated from one or more medical imaging devices 10 such as magnetic resonance (MR), positron emission tomography (PET) and the like. The medical images are stored in a data store 12. The medical images can be 2D such as 2D slices of a volume, 3D volumes, and the like. The images are spatially registered. For example, a global rigid 3D transformation is used for intracranial imaging. The data store can be local memory, disk, network attached storage, and the like. The one or more medical images includes a first contrast 14 indicative of a tumor tissue such as vital tumor tissue, and a second contrast 16 indicative of related tumor tissue such as peri-focal tissue. For example, MR T1 Contrast Enhanced (T1CE) contrasts vital tumor tissue as hyperintense and MR Fluid Attenuated Inversion Recovery (FLAIR) contrasts perifocal edema as hyper-intense. Other MR protocols and contrasts include T1, T2, Magnetization of Prepared Rapid Gradient Echo (MPRAGE), Vascular Space Occupancy (VASO), and the like. The data store and medical imaging device connect by a network 18. The network can be direct or indirect, wired or wireless, private or public such as the Internet, or any combination.

A workstation 20 connects to the network 18 and a healthcare practitioner selects a seed or starting point from the first contrast using at least one input device 22. The workstation 20 includes an electronic processor or electronic processing device 24, a display 26 which displays the first and/or second contrast, menus, panels, and user controls, and the at least one input device 22 which inputs the healthcare practitioner selections. The workstation 20 can be a desktop computer, a laptop, a tablet, a mobile computing device, a smartphone, and the like. The input device can be a keyboard, a mouse, a microphone, and the like. The seed location selected on the displayed contrast is converted by a user interface module 28 to a voxel location.

The user interface module 28 processes healthcare practitioner input via at least one input device relative to the display displayed by the display device. The displays can include menus, panels, web pages, user controls, parameters selections, and the like.

A coarse segmenter 30 creates coarse voxels which include an aggregation of voxels and a maximum and a minimum of the voxel intensities of the aggregated voxels. The coarse segmenter 30 grows a coarse segmented region of coarse voxels for each contrasted tissue type from the seed location based on a growing algorithm and a growing fraction for each contrast. The algorithm iterates with a starting growing fraction for a coarse segmented region and increments the growing fraction until the grown region contains the seed. The seed location for the second contrasted tissue type includes the coarse segmented region for the first contrasted tissue type and any fully enclosed coarse voxels. The volume of either of the co-registered images of the first and second contrast can be used or a corresponding volume. The coarse segmenter transfer the results from one space through an appropriate transform.

A fine segmenter 32 grows a segmented region of voxels for each contrasted tissue type from the seed location based on a second growing algorithm and an adjustable growing fraction for each segmented region. The segmented regions are bounded by the coarse segmented region grown for the second contrasted tissue type. The seed location for the second contrast includes a first segmented region from the first contrast. The adjustable growing fractions are initially the final values from the corresponding final coarse growing fractions.

An enclosed tissue identification module 34 identifies any fully enclosed voxels in the first segmented region. The fully enclosed voxels represent a third related tissue type such as necrotic tissue. In an option, the healthcare practitioner selects with an input device a ray-search in the users controls displayed by the display device. The enclosed tissue identification module performs a ray search on nearly enclosed voxels by the first segmented region. The region uses vectors projected in multiple directions and rotated to determine nearly enclosed. For example, if vectors of a voxel projected in eight directions, rotated 22.5° and projected in again in eight directions, encounter the first segment region, then the voxel is classified as the third tissue type. The ray search option is useful for instances where vital tumor tissue includes a thin rim of the first contrast which may not be contrasted sufficiently for the growing algorithms to identify.

The final segmentation and tissue identification can be displayed and/or stored in a storage management system 35 such as a Picture Archiving and Communication System (PACS), a Radiology Information System (RIS), and the like. Multiple results can be displayed and/or stored such as multiple seed locations or tumors, different growing parameters and/or search parameters, and the like.

The various segmenters or modules 30, 32, 34 are suitably embodied by an electronic data processing device, such as the electronic processor or electronic processing device 24 of the workstation 20, or by a network-based server computer operatively connected with the workstation 20 by the network 18, or so forth. The user interface module 28 is suitably embodied by the workstation 20. Moreover, the disclosed segmentation and tissue identification techniques are suitably implemented as a non-transitory storage medium storing instructions (e.g., software) readable by an electronic data processing device and executable by the electronic data processing device to perform the disclosed segmentation and tissue identification techniques.

FIG. 2A-B schematically illustrates several examples of coarse voxel construction performed by the coarse segmenter. In a first example of FIG. 2A, the coarse voxel is constructed from a cubic volume of voxels such as volume 3×3×3 mm. Each voxel includes a single intensity value. The coarse voxel is characterized by two intensity values: a minimum and a maximum of the intensities of all voxels aggregated to form the coarse voxel. The two values of the coarse voxel define the range of values for the aggregated voxels. These two values are different from an average or an interpolated value typically used in other approaches. The range of values reduces the information lost in aggregation while improving the computational performance. The volume preferred includes an incremental volume of an integer number of voxels and fractional voxels are avoided. The volume can be otherwise sized than 3×3×3 mm, and additionally other regularly dimensioned shapes such as rectangular prism, rectangular cuboid, and the like are contemplated.

In a second example of FIG. 2B, the coarse voxel is constructed from a slice of voxels. The slice of voxels can be represented as 2D pixels. For example, with a slice thickness of 5 mm, a pixel spacing of 0.449×0.449 mm, and a slice gap of 1 mm, the coarse segmenter can create a coarse voxel with a 6×6 plane of pixels. The coarse voxel can be constructed of any regularly dimensioned pattern which includes the complete 2D sliced volume.

FIG. 3 diagrammatically illustrates one example of the various segmented volumes and optional ray search. The coarse segmenter segments the first coarse region with the first contrast and the seed 37 within the first contrast which approximates the volume or area of vital tumor tissue. The seed 37 include a point within the first contrast. The first coarse region includes coarse voxels which are fully enclosed and include volumes or areas of necrotic tissue. For example, the first coarse segmented region includes areas label A and C.

In the growing algorithm, initially the first coarse region includes the coarse voxel of the seed. The maximum of the first coarse region is the maximum of the coarse voxel included. The minimum of the first coarse region is the first growing fraction of the maximum of the first coarse region. For example, with a growing fraction of 0.6 and a maximum of 100, the minimum of the first coarse region is 60. Neighboring coarse voxels are searched and added to the first coarse region if the maximum of the coarse voxel searched exceeds the minimum of the first coarse region. If the maximum of the coarse voxel added exceeds the maximum of the first coarse region, then the maximum of the first coarse region becomes the maximum of the added coarse voxel, a new minimum is calculated based on the growing fraction, and the region growing is restarted with the location of the new maximum as seed. If a coarse voxel is added to the first coarse region and the minimum value of the coarse voxel is less than the minimum value of the first coarse region, then the coarse voxel added is excluded for the search space of neighboring regions. The instance of the coarse voxel minimum less than the minimum of the first coarse region suggests that some voxels do not include the tissue type of the first contrast. The growing algorithm iteratively searches neighboring regions, adds coarse voxels adapting the upper and lower bounds until no more coarse voxels are available to be added. When the growing algorithm completes an iteration, the first coarse region is checked for inclusion of the seed. If the first coarse region does not contain the seed, then the growing fraction is incremented, e.g. starting with 0.4 and incrementing 0.05. Not containing the seed in the first coarse region grown indicates that leakage occurred. The growing restarts with the original seed and the incremented growing fraction. The algorithm ends once the first coarse region grown contains the original seed or a maximum growing fraction is reached such as 0.7. The coarse segmenter 30 is made computationally efficient by using coarse voxels. The use of coarse voxels as disclosed also avoids leakage due to small connecting bright bands containing unrelated neighboring structures.

In the illustrative example of tumor segmentation, it is desired to segment both the vital tumor and its surrounding edema. To accomplish this, the coarse segmenter 30 is applied again to segment a second coarse region beginning with the areas A and C (the coarse segmentation of the vital tissue A and enclosed necrotic tissue C) and extending to include approximately the area labeled B (corresponding to the edema). Since the edema is expected to surround the vital tissue which in turn is expected to enclose any necrotic tissue that may be present, the areas A and C suitably serve as the seed for the segmentation of the second coarse segmented region (i.e., the edema). The second coarse segmented region of areas A-C is grown using the same algorithm as the first coarse region except for a different seed and a second growing fraction. Also, in the illustrative example the first segmentation is performed in a T1CE image that provides hyper-intense contrast for the vital tissue, while the second segmentation is performed in a FLAIR contrast image which provides hyper-intense contrast for the edema. In the second segmentation, the growing fraction is for instance initially set to 0.35 and incremented in 0.05 increments. Fully enclosed coarse voxels are not added to the second coarse segmented region. The second coarse region defines the boundary of the growing algorithm used by the fine segmenter. For example, the area D beyond the second coarse region becomes a masked region for the fine segmenter.

The coarse segmentation performed by the coarse segmenter 30 is followed by finer (i.e. higher resolution) segmentation performed by the fine segmenter 32. The fine segmenter refines the first coarse region to the first segmented region with a second growing algorithm, the original seed, an adjustable growing fraction, and the second coarse region as a boundary or mask for growth. Growth during fine segmentation is by voxel rather than by coarse voxel (as was the case in coarse segmentation). A voxel has only one value.

The fine segmenter 32 grows the first segmented region from the original seed to a refined or first segmented region, which is expected to be a higher resolution segmentation of the area A. A first adjustable growing fraction sets the lower bound for the growing algorithm and is initially set to the final growing fraction of the first coarse region. The segmented region begins with the original seed with a maximum value equal to the intensity of the seed voxel and a minimum value equal to the first adjustable growing fraction of the maximum value. Voxels in a neighboring region to the segmented region are searched, wherein the neighboring region excludes any voxels outside the second coarse region or in the masked region B. Searched voxels are added to the segmented region if the value of the searched voxel exceeds the minimum value of the segmented region. For voxels added to the segmented region, the maximum of the segmented region is revised to include the greater of the maximum of the added voxel and the segmented region, and the minimum of the segmented region is revised as a growing fraction of the maximum of the segmented region. If the maximum is changed, the region growing is restarted with the location of the new maximum as seed. The process of searching and adding voxels is repeated until no more voxels are available to be added to the segmented region.

The enclosed region identification module 34 identifies the enclosed area and (if selected) any nearly enclosed areas. The enclosed areas include voxels fully enclosed by voxels in the first segmented area. If a ray search is selected, then a ray search is used to discover and identify voxels nearly enclosed by the first segmented region such as the region labeled E.

In similar fashion, the fine segmenter 32 grows the second segmented region (e.g., in the FLAIR image) to segment the edema starting from a seed which includes the first segmented region, the fully enclosed voxels, and if identified, the nearly enclosed voxels. A second adjustable growing fraction is used initially set to the final second growing fraction. The boundary or mask for the second segmented region is the second coarse region. The second adjustable growing fraction sets the lower bound for the growing algorithm. The segmented region begins with the first segmented region as seed with a maximum value equal to the intensity of the seed voxels and a minimum value equal to the second adjustable growing fraction of the maximum value. Voxels in a neighboring region to the segmented region are searched, wherein the neighboring region excludes any voxels outside the second coarse region or in the masked region D. Searched voxels are added to the segmented region if the value of the searched voxel exceeds the minimum value of the segmented region. For voxels added to the segmented region, the maximum of the segmented region is revised to include the greater of the maximum of the added voxel and the segmented region, and the minimum of the segmented region is revised as the second adjustable growing fraction of the maximum of the segmented region. The process of searching and adding voxels is repeated until no more voxels are added to the segmented region.

The healthcare practitioner preferably reviews the segmented regions, and through the user interface optionally modifies the adjustable growing fractions and/or search ray. If such manual adjustments are made, then the fine segmenter 32 uses the modified adjustable growing fractions and/or search ray to grow new regions with the second algorithm, the original seed, the adjustable growing fractions, and the second coarse region as the mask.

FIG. 4 illustrates an example user interface displayed by the display device. The user interface module creates the display and processes the input relative to the display from the one or more input devices. The healthcare practitioner interacts with the user interface module through the user interface, display device, and input device to fine tune the regions segmented by the second growing algorithm.

The user interface module includes selection of data sets and/or specific images for segmentation 48 based on standard conventions. The selection can include a 3D volume or a 2D slice of a 3D volume. Image controls 50 allow the user to manipulate the images. For example, a slider bar control can move the display through the image volume or between slices, a transparency control can permit image overlays, a radio button can permit selection of the manipulated imaging data set. The selection can include a single image with multiple contrasts, multiple images with single contrast, or multiple images with multiple contrasts.

The healthcare practitioner identifies a specific location in one displayed image 46 and through one of the input devices indicates the seed. The seed selection includes a point of hyper-intensity. The image is re-displayed with the segmented and identified regions contrasted such as a color enhancement for each segmented and identified region. For example, vital tumor tissue is displayed in red, edema tissue displayed in green, and necrotic tissue displayed in blue. With the image re-display, a growing fraction control 52, 54 for each segmented region is displayed. The displayed growing fraction controls can include slider bars, etc. and be normalized. For example, the adjustable growing fraction in current use is displayed as 0 and centered in the slider bar. The healthcare practitioner moves the slider bar left or right to decrease or increase the size of the region grown. A movement to the left or decrease in region size increases the adjustable growing fraction for the contrast. Similarly, a movement to the right can be indicative of desire to increase the growing region, and the adjustable growing fraction is correspondingly decreased. Each segmented region includes a separate user control for the adjustable growing fraction for the region.

The optional ray search can be turned on and off by the healthcare practitioner such as clicking to check or uncheck a checkbox 56. The turned on ray search identifies nearly enclosed tissue (for example, the nearly enclosed region E in FIG. 3) and classifies the nearly enclosed tissue such as necrotic tissue. The identified nearly enclosed tissue is added to the seed location for the second segmented region.

The user interface saves the final diagnostic image which includes the segmented regions and identified tissue types. The saved information includes the same geometry as the image contrasts, but each voxel in a segmented region or identified tissue type includes a intensity value of the segmented or identified tissue type such as 0 for background, 1365 for necrosis, 2730 for edema, and 4095 for vital tumor tissue. The healthcare practitioner can select another area indicative of a tumor and a new set of regions are grown with the selected area as the seed location.

With reference back to FIG. 1 and with further reference to FIG. 5, one method of using an embodiment of the segmentation and tissue identification is flowcharted. The imaging data sets are selected in a step 60. The imaging data sets can include two images each with a separate contrast such as a T1CE image contrasting vital tumor tissue, and a FLAIR image contrasting edema tissue. In a step 62, the healthcare practitioner moves through the image or images and selects a seed location which indicates a tumor.

In a step 64, the coarse segmenter 30 iteratively grows the first coarse segmented region using the first growing algorithm and the first growing fraction. The processor performing the coarse segmentation can be transparent to the healthcare practitioner. In a step 66, the coarse segmenter adds the fully enclosed coarse voxels to the first coarse segmented region. This first coarse segmentation is suitably performed in the T1CE image and provides coarse delineation of the vital tissue.

The coarse segmenter, in a step 68, similarly grows the second coarse segmented region. The seed for the second coarse region includes the first coarse region. The first growing algorithm operates with the second growing fraction to grow the second coarse region. The second coarse region becomes the mask for the fine segmenter. The second coarse segmentation is suitably performed in a FLAIR image and provides coarse delineation of the edema.

The fine segmenter 32, in a step 70, grows the first segmented region with the original seed, the first adjustable growing fraction initially set to the final first growing fraction, and the second growing algorithm. The first segmented region includes the first tissue type such as vital tumor tissue. This first fine segmentation is suitably performed in the T1CE image and provides fine delineation of the vital tissue.

The enclosed tissue identification module 34, in a step 72, identifies any voxels fully enclosed by the first segmented region. These enclosed regions are expected to correspond to necrotic tissue. If the ray search is selected as indicated in a decision step 74, then any voxels nearly enclosed by the first segmented region are identified in a step 76. The fully enclosed voxels, and if selected, the nearly enclosed voxels include the identified tissue type such as necrotic tissue.

In a step 78, the fine segmenter grows the second segmented region with the seed including the first segmented region and any identified tissue type. The fine segmenter grows the second segmented region with the seed, the second adjustable growing fraction initially set to the final second growing fraction, the second growing algorithm, and the second coarse segmented region as the mask or boundry for growth. The second fine segmentation is suitably performed in a FLAIR image and provides fine delineation of the edema.

The results output by the fine segmenter 32 and the enclosed tissue identification module 34 are displayed by the user interface module 28 in a step 80. The segmented regions and identified tissue types are displayed with visually perceptible delineations such as with different colors. The healthcare practitioner can review the regions segmented and/or identified with the user controls, and optionally change the adjustable growing fractions or use of the ray search. Changes made by the healthcare practitioner through the user interface are interpreted in a step 82 and restart the process beginning with the fine segmentation of the first segmented region. Alternatively the healthcare practitioner can store the results in the storage management system in a step 84. Another alternative includes selection of a different seed location in a step 86 which restarts the process with selecting the seed location, followed by coarse segmentation.

With reference to FIG. 6, the algorithm for coarse segmentation implemented by the coarse segmenter 30 is flowcharted. In a step 88, the growing region or coarse segmented region is initialized to the seed. The search region is initialized. An initial growing fraction is selected based on the image type, default value, and the like. In a step 90, the neighboring coarse voxels are searched.

If a coarse voxel is found in a step 92 which includes a maximum which exceeds the minimum for the coarse region segmented thus far, then the coarse voxel is added to the coarse region in a step 94. The minimum of the coarse voxel to be added is compared in a step 92. If the coarse voxel minimum is lower than the minimum for the coarse region, then in a step 94, the coarse voxel is excluded from the search criteria. In a step 96, the maximum of the coarse voxel to be added is compared with the maximum of the coarse region segmented thus far. If the maximum of the coarse voxel to be added exceeds the maximum of the coarse region, then the coarse region maximum is set to the maximum of the coarse voxel to be added in a step 98. If the maximum of the coarse region is changed, then the minimum is computed as the maximum times the growing fraction in a step 100, and the region growing is restarted with the coarse region reinitialized to the location of the new maximum as the seed in a step 102. The process repeats from the search of neighboring coarse voxels 90 until all coarse voxels are added.

If no more coarse voxels are available to be added, then in a step 104, the coarse segmented region is inspected to verify inclusion of the seed. If the seed is not contained in the coarse segmented region, then the growing fraction is incremented in a step 106, and the segmented region and search region reset to the seed in a step 108. After incrementing the growing fraction and resetting the seed, the algorithm regrows the segmented region beginning with the search of neighboring coarse voxels. The coarse segmented region is iteratively regrown incrementing the growing fraction until the seed is contained in the coarse segmented region or the growing fraction reaches a maximum such as 0.70. The final coarse segmented region and the final growing fraction is returned 110.

With reference to FIG. 7, the algorithm for fine segmentation is flowcharted. In a step 112, the segmented region is initialized and the adjustable growing fraction input. The adjustable growing fraction is set to the final corresponding growing fraction unless modified by the healthcare practitioner. The neighboring voxels are searched in a step 114. Voxels outside the second coarse segmented region are excluded from the search. The algorithm continues if voxels are available to be added in a step 116, otherwise the segmented region is returned 128.

Voxels of an intensity which exceeds the minimum of the segmented region are included in the segmented region in a step 118. The intensity voxel to be added is compared with the maximum of the segmented region in a step 120, and if the voxel intensity exceeds the maximum of the segmented region before adding, then in a step 122 the maximum of the region is updated to the voxel intensity, and a new minimum of the segmented region or growing region is computed in a step 124 as the region maximum times the adjustable growing fraction. All voxels found in the search are added, and the process is repeated beginning with the search until no voxels are added to the segmented region. The segmented region is returned.

The illustrative examples pertain to segmenting a tumor expected to comprise vital tumor tissue (possibly containing some necrotic regions) surrounded by an edema. To segment both the vital tissue and edema, the coarse and fine segmentation processes are each run twice, with the second run using the vital tissue delineated by the first run as the seed. In some other applications, no outer structure corresponding to the edema may be present—in such cases, a single coarse region growing process is followed by a single fine region growing process (the latter optionally repeated to include any received user adjustments). The illustrative examples employ a T1CE image to provide hyper-intense contrast for vital tumor tissue, and a FLAIR image to provide hyper-intense contrast for the edema. In some other applications, a single image may provide both contrasts in which case the vital tumor tissue and edema tissue segmentations may be performed on the single image. As yet another contemplated variation, while in the illustrative embodiments the region growing fraction and maximum intensity are used as tunable parameters for adjusting the coarse segmentation to avoid leakage, it is additionally or alternatively contemplated to adjust the size and/or shape of the coarse voxels for this purpose.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

The invention claimed is:

1. A medical imaging system, comprising:
   a workstation including:
      at least one input which receives a selected location in an imaging data set having different contrast for a first and a second contrasted tissue type as a seed in the first contrasted tissue type; and
      a display which displays a diagnostic image delineating a first segmented region of the first tissue type and a second segmented region of the second contrasted tissue type and identified regions which include regions fully enclosed by the first segmented region as a third tissue type;
   a coarse segmenting processor programmed to perform a first segmenting operation including growing a coarse segmented region of coarse voxels for each contrasted tissue type from the seed location based on a first growing algorithm and a growing fraction for each contrasted tissue type, wherein the seed location for growing the second contrasted tissue type includes the first coarse segmented region and any fully enclosed coarse voxels, and each coarse voxel includes an aggregation of voxels and a maximum and a minimum of the voxel intensities;
   a fine segmenting processor programmed to perform a second segmenting operation including growing a segmented region of voxels for each contrasted tissue type from the seed location and bounded by the second coarse segmented region based on a second growing algorithm and an adjustable growing fraction for each contrasted tissue type initially set to the growing fraction for the corresponding region, wherein the seed location for growing the second contrasted tissue type includes the first segmented region and any identified regions; and
   an enclosed tissue identification processor programmed to identify any regions of voxels fully enclosed by the first segmented region as being of the third tissue type;
   wherein the coarse segmenting processor, the fine segmenting processor, and the enclosed tissue identification processor are implemented by an electronic data processor.

2. The medical imaging system according to claim 1, wherein the coarse segmenting processor is configured to grow the coarse segmented region by:
   searching the coarse voxels in a region neighboring the coarse segmented region; and
   adding each searched coarse voxel to the coarse segmented region if the maximum value of the searched coarse voxel exceeds the minimum value of the coarse segmented region; and
   when adding the searched coarse voxel to the coarse segmented region:
      updating the maximum of the coarse segmented region to the larger of the maximum of the added coarse voxel and the maximum of the coarse segmented region;
      if the maximum is the maximum of the added course voxel, then updating the minimum of the coarse segmented region as the growing fraction of the updated maximum of the coarse segmented region and restarting the region growing with the location of the new maximum as the seed; and
   revising the search to exclude added coarse voxels with minimum values lower than the updated minimum value of the coarse segmented region.

3. The medical imaging system according to claim 1, wherein the fine segmenting processor is configured to grow the segmented region by:
   searching voxels in a region neighboring the segmented region, wherein the neighboring region excludes voxels outside a bounded region defined by the coarse segmenting processor;
   adding each searched voxel to the segmented region if the value of the searched voxel exceeds the minimum value of the segmented region; and
   when adding the searched voxel to the segmented region:
      updating the maximum of the segmented region to include the greater of the value of the added voxel and the maximum value of the segmented region; and
      revising the minimum of the segmented region as the adjustable growing fraction of the updated maximum of the segmented region.

4. The medical imaging system according to any claim 1, wherein:
   the display further displays user selectable controls for input of the adjustable growing fraction for each segmented region;
   wherein the fine segmenting processor regrows the segmented regions based on the input adjustable growing fraction for each segmented region.

5. The medical imaging system according to claim 1, wherein the first contrasted tissue type includes vital tumor tissue and the second contrasted tissue type includes edema tissue and the third tissue type include necrotic tissue and the displayed diagnostic image contrasts the tissue types.

6. The medical imaging system according to claim 1, wherein the enclosed tissue identification processor is configured to:
   search for regions nearly enclosed by the segmented region of the first contrasted tissue type based on a ray search and identify any nearly enclosed regions as the third tissue type.

7. The medical imaging system according to claim 1, wherein the seed location has the contrast indicative of a tumor.

8. The medical imaging system according to claim 1, wherein the at least one imaging data set includes at least one of:
- a T1 contrast enhanced magnetic resonance image;
- a fluid attenuated inversion recovery magnetic resonance image; and
- a positron emission tomography image.

9. The medical imaging system according to claim 1, wherein the at least one imaging data set includes:
- a T1 contrast enhanced magnetic resonance image wherein the first segmented region of the first tissue type comprises a first segmented region of vital tumor tissue; and
- a fluid attenuated inversion recovery magnetic resonance image wherein the second segmented region of the second tissue type comprises a second segmented region of edema tissue.

10. The medical imaging system according to claim 1, wherein the at least one imaging data set includes multi-contrast magnetic resonance brain images.

11. A method, comprising:
- performing a coarse region growing algorithm to define a coarse segmented region in an image, the coarse region growing algorithm operating on coarse voxels of the image where each coarse voxel is an aggregation of voxels characterized in the coarse region growing algorithm by the maximum voxel value of the aggregation of voxels and the minimum voxel value of the aggregation of voxels;
- performing a fine region growing algorithm to define a segmented region in the image, the fine region growing algorithm operating on voxels of the image and being constrained by a growth bound defined by the coarse segmented region; and
- displaying the segmented region on a display;
- wherein the performing operations are performed by an electronic data processor.

12. The method of claim 11, wherein:
- the coarse region growing algorithm adds a coarse voxel to the coarse segmented region if the maximum voxel value of the coarse voxel exceeds a threshold voxel value; and
- the coarse region growing algorithm uses the added coarse voxel for further growth of the coarse segmented region if the minimum voxel value of the coarse voxel exceeds the threshold voxel value.

13. The method of claim 12, wherein the coarse region growing algorithm computes the threshold voxel value as a selected fraction of the maximum of the maximum voxel values of coarse voxels making up the coarse segmented region.

14. The method of claim 11, wherein the image includes a T1 contrast enhanced (T1CE) magnetic resonance image and a fluid attenuated inversion recovery (FLAIR) magnetic resonance image, and the method comprises:
- performing the coarse region growing algorithm on the T1CE image to coarsely delineate vital tumor tissue;
- performing the coarse region growing algorithm on the FLAIR image to coarsely delineate edema tissue;
- performing the fine region growing algorithm on the T1CE image to delineate vital tumor tissue constrained by a boundary defined by the coarsely delineate edema tissue; and
- performing the fine region growing algorithm on the FLAIR image to delineate edema tissue constrained by a boundary defined by the coarsely delineate edema tissue.

15. The method of claim 14, wherein:
- the performing of the coarse region growing algorithm on the FLAIR image uses a seed comprising the coarsely delineated vital tumor tissue; and
- the performing of the fine region growing algorithm on the FLAIR image uses a seed comprising the delineated vital tumor tissue.

16. The method of claim 14, further comprising:
- identifying any regions of voxels fully enclosed by the delineated vital tumor tissue as being of necrotic tissue, the identifying being performed by an electronic data processing device.

17. A non-transitory computer-readable medium carrying software which controls one or more electronic data processing devices to perform a method as set forth in claim 11.

18. An electronic data processor configured to perform a method as set forth in claim 11.

19. A medical imaging system, comprising:
- an electronic data processor programmed to perform operations including:
  - segmenting a T1 contrast enhanced (T1CE) magnetic resonance image of an imaging subject to define a segmented region comprising vital tumor tissue; and
  - segmenting a fluid attenuated inversion recovery (FLAIR) magnetic resonance image of the imaging subject using region growing to define a segmented region comprising edema tissue wherein the segmented region comprising vital tumor tissue serves as the seed for the region growing.

20. The medical imaging system of claim 1, wherein the electronic data processor is further programmed to:
- perform the first and second segmenting operations a first time operating on coarse voxels of the T1 contrast enhanced and fluid attenuated inversion recovery images wherein a coarse voxel is an aggregation of voxels characterized by the maximum voxel value of the aggregation of voxels and the minimum voxel value of the aggregation of voxels; and
- perform the first and second segmenting operations a second time operating on voxels of the T1 contrast enhanced and fluid attenuated inversion recovery images wherein the segmented region comprising edema tissue defined by the first segmenting operation performed on the fluid attenuated inversion recovery image serves as a constraining boundary for the second segmenting operations.

\* \* \* \* \*